US006933301B2

(12) United States Patent
Wei

(10) Patent No.: US 6,933,301 B2
(45) Date of Patent: Aug. 23, 2005

(54) 1,2,3,6-TETRAHYDROPYRIMIDINE-2-ONE COMPOSITIONS, ARTICLES AND THERAPEUTIC METHODS FOR UPPER AIRWAY BREATHING DISORDERS

(76) Inventor: Edward T. Wei, 480 Grizzly Peak Blvd., Berkeley, CA (US) 94708

( * ) Notice: Subject to any disclaimer, the term of this patent is extended or adjusted under 35 U.S.C. 154(b) by 360 days.

(21) Appl. No.: 10/267,896

(22) Filed: Oct. 8, 2002

(65) Prior Publication Data

US 2003/0206866 A1 Nov. 6, 2003

Related U.S. Application Data

(63) Continuation-in-part of application No. 10/139,193, filed on May 2, 2002.

(51) Int. Cl.$^7$ ...................... A61K 31/513; A61K 38/18; A61K 31/47; C07D 241/40; C07D 215/16
(52) U.S. Cl. ...................... 514/269; 514/345; 514/311; 514/312; 514/313; 514/314; 544/318; 546/153; 546/159; 546/171; 546/178; 546/179
(58) Field of Search ................................ 514/269, 345, 514/318, 311, 312, 313, 314; 546/153, 159, 171, 178, 179

(56) References Cited

U.S. PATENT DOCUMENTS

| | | | |
|---|---|---|---|
| 3,821,221 A | | 6/1974 | Podesva et al. |
| 3,947,439 A | * | 3/1976 | Wei et al. .................. 544/250 |
| 5,116,868 A | | 5/1992 | Chen et al. |
| 5,215,221 A | | 6/1993 | Dirksing |
| 5,582,330 A | | 12/1996 | Iba |
| 5,800,485 A | | 9/1998 | Trop et al. |
| 5,942,545 A | | 8/1999 | Samour et al. |
| 6,098,619 A | | 8/2000 | Britto et al. |
| 6,166,044 A | | 12/2000 | Sandborn et al. |
| 6,245,760 B1 | * | 6/2001 | He et al. ................. 514/234.8 |
| 6,319,513 B1 | | 11/2001 | Dobrozsi |
| 6,365,190 B1 | | 4/2002 | Gordon et al. |
| 6,391,869 B1 | | 5/2002 | Parks et al. |
| 6,436,950 B1 | | 8/2002 | Achari |
| 6,443,152 B1 | | 9/2002 | Lockhart et al. |
| 6,482,834 B2 | * | 11/2002 | Spada et al. ................ 514/311 |
| 6,743,801 B2 | * | 6/2004 | Wei ............................ 514/269 |
| 6,797,725 B2 | * | 9/2004 | Sun et al. .................... 514/414 |
| 2001/0023250 A1 | * | 9/2001 | Spada et al. ................ 514/250 |
| 2003/0100555 A1 | * | 5/2003 | Sun et al. ................ 514/232.8 |
| 2003/0206866 A1 | * | 11/2003 | Wei ............................. 424/45 |
| 2003/0206873 A1 | * | 11/2003 | Wei ............................. 424/48 |
| 2003/0207851 A1 | * | 11/2003 | Wei ............................ 514/171 |
| 2003/0207903 A1 | * | 11/2003 | Wei ............................ 514/269 |
| 2003/0207904 A1 | * | 11/2003 | Wei ............................ 514/269 |
| 2004/0186161 A1 | * | 9/2004 | Sun et al. .................... 514/414 |

OTHER PUBLICATIONS

Babes, et al, Cooling inhibits capsaicin . . . Neuroscience Letters 317: 131–134; 2002.
Barnes P.J. Neurogenic inflammation in the airways. Respiratory Physiology 125: 145–154, 2001.
Dykewicz et al, Annals Allergy Asthma Immuno. 81:pp478–518 (1998).
McKemy et al, Identification of a cold receptor reveals a general role for TRP channels in thermosensation. Nature 416: 52–58, 2002.
Nair, , Chpt 39, Solutions, Emulsions, Suspensions and Extracts, pp721–752, in Remington, the Science and Practice of Pharmacy, 20$^{th}$ ed, Lippincott, Williams & Wilkins, 2000.
Sciarra and Sicarra, Chpt 50, Aerosols, pp963–979, , in Remington, the Science and Practice of Pharmacy, 20$^{th}$ ed, Lippincott, Williams & Wilkins, 2000.
Wei, E.T. Chemical stimulants of shaking behavior. Journal Pharmacy and Pharmacology 28: 722–724, 1976.
Wei, E.T. Pharmacological aspects of shaking behavior produced by AG–3–5, TRH, and morphine withdrawal. Federation Proceedings 40: 1491–1496, 1981.
Wei, E.T. and D.A. Seid. AG–3–5: A chemical producing sensations of cold. Journal Pharmacy and Pharmacology 35: 110–112, 1983.
Scharf and Cohen, Annals Allergy Asthma Immuno 81: pp279–290 (1998).
O'Connor and Schwartz, Powders, Chpt 37, pp 681–699, in "Remington, the science and practice of pharmacy", 20$^{th}$ ed. Lippincott Williams & Wilkins, 2000.
http://www.tocris.com/shop/dispprod.php?itemid=38283 (Icilin), printed Oct. 1, 2002.

* cited by examiner

Primary Examiner—Sabiha N. Qazi

(57) ABSTRACT

A therapeutic composition is provided that comprises a 1-R1-phenyl, 4-R2-phenyl substituted 1,2,3,6-tetrahydropyrimidine-2-one cold receptor agonist in a therapeutically effective amount. The cold receptor agonist may be represented by the general formula 1-[R1-phenyl]-4-[R2-phenyl]-1,2,3,6-tetrahydropyrimidine-2-one wherein: R1 is -hydroxy, -chloro, -fluoro, -alkyl, -acetoxy, -trifluoromethyl; and R2 is -nitro, -chloro, -fluoro, -alkyl, -trifluoromethyl. Therapeutic compositions of the invention when formulated for delivery to the mucous membranes of the nose and throat alleviate the sensations of airway obstruction and provide symptomatic relief of upper airway breathing disorders.

5 Claims, No Drawings

1,2,3,6-TETRAHYDROPYRIMIDINE-2-ONE COMPOSITIONS, ARTICLES AND THERAPEUTIC METHODS FOR UPPER AIRWAY BREATHING DISORDERS

CROSS-REFERENCE TO RELATED APPLICATIONS

This application is a continuation-in-part of Ser. No. 10/139,193, filed May 2, 2002, inventor Wei, entitled "Therapeutic 1,2,3,6-Tetrahydropyrimidine-2-One Compositions and Methods Therewith", incorporated by reference.

STATEMENT REGARDING FEDERALLY SPONSORED RESEARCH OR DEVELOPMENT

Not applicable.

BACKGROUND OF THE INVENTION

1. Field of the Invention

The invention generally relates to apparatus and therapeutic compositions useful to relieve breathing disorders of the upper airways. This invention more particularly relates to a class of chemicals that activate cold receptors on the mucous membranes of the nose and throat, articles and compositions including these chemicals, and therapeutic uses of these chemicals for relief of nasal and throat discomfort due to inflammation and pain. The particularly preferred embodiment compositions are formulated so as to be delivered as droplets or powder, and comprise "icilin", a 1,2,3,6-tetrahydropyrimidine-2-one compound.

2. Description of Related Art

Background on icilin compounds. 1,2,3,6-Tetrahydropyrimidine-2-one compounds were described in U.S. Pat. No. 3,821,221(inventors C. Podesva and J. M. Do Nascimento et al., Jun. 28, 1974). These compounds were thought to have depressant and/or stimulant effects on the central nervous system. In 1972, an abstract described a compound in this series called AG-3-5 (1[2-hydroxyphenyl]-4-[3-nitrophenyl]-1,2,3,6-tetrahydropyrimidine-2-one). This prototype elicited a syndrome of "wet dog shake behavior" in rats and monkeys accompanied by hyperthermia, hyperactivity and ptosis. Wei (Chemical stimulants of shaking behavior. Journal of Pharmacy and Pharmacology 28: 722–724, 1976) provided the first detailed report of the actions of AG-3-5 in animals and noted that shaking behavior similar to those of a dog when wet could be evoked in various laboratory animals such as the rat, mouse, cat, dog, gerbils, guinea pigs and hamsters.

Subsequently, Wei (Pharmacological aspects of shaking behavior produced by AG-3-5, TRH, and morphine withdrawal. Federation Proceedings 40: 1491–1496, 1981) reported that 0.1 mg of AG-3-5, dissolved in propylene glycol, applied to the dorsum of the tongue elicited prickling sensations of cold and ingestion of 6 mg mixed in orange juice, on one occasion out of three, produced sensations of coolness on the cheeks and on the inner surfaces of the arms and legs. It was hypothesized that AG-3-5 may produce specific activation of receptors for cold, and that stimulation of these receptors accounted for the shaking seen in laboratory animals. In a subsequent publication (E. T. Wei and D. A. Seid. AG-3-5: A chemical producing sensations of cold. Journal of Pharmacy and Pharmacology 35: 110–112, 1983) the effects of AG-3-5 on shaking behavior in the rat were compared to those of menthol and AG-3-5 was shown to be 400 times more potent than menthol on a molar basis on this behavioral endpoint. AG-3-5 was less toxic than menthol, as measured by the oral median lethal dose in rats.

AG-3-5 was named icilin by Wei because of its cold-producing properties. Icilin has recently become commercially available from Tocris Cookson Inc., Ellisville, Mo. 63021 and Phoenix Pharmaceuticals, Belmont, Calif., USA.

Recently, two independent groups simultaneously cloned a biological macromolecule (called a receptor) from trigeminal sensory neurons of the rat. These receptors belong to the transient receptor potential (TRP) family of ion channels and respond to cold temperature and to menthol. Using a sample provided by Wei, McKemy et al. (Identification of a cold receptor reveals a general role for TRP channels in thermosensation. Nature 416: 52–58, 2002) showed that icilin was about 200 times more potent than menthol in eliciting ion channel current changes in the cloned and transfected TRP(M8) receptor. The ion permeability changes elicited in transfected cells were more robust with icilin than those elicited by menthol, and the presence of extracellular calcium was required for activity. Menthol currents did not require extracellular calcium.

The chemical structure of icilin bears little similarity to that of menthol; the former chemical being a pyrimidine-2-one attached to two phenyl rings, and the latter a cyclohexanol derivative. Activation of the TRP(M8) receptor on the neuronal membrane may lead to depolarization of the sensory nerve ending and send action potentials towards the spinal cord and brain that are eventually recognized as psychic signals of skin stimulation. The term "agonist" is used by pharmacologists to denote a chemical substance that activates biological events. Hence, icilin and its analogs may be classified as "cold receptor agonists."

Background on treatment of nasal and upper airway irritation, stuffiness, and congestion. The nose is the entrance to the respiratory tract. It serves as a conduit for inspired and expired air. When one or both sides of the nose are obstructed, this impairs nasal functioning and is perceived as an uncomfortable condition. All the nasal cavity bony surfaces, including the paranasal sinuses, are lined by tissue called mucosa. This mucosa contains blood vessels, nerves, and small glands that secrete mucus and fluids into the nasal cavity. The nose is also richly supplied by sensory nerves that detect pain, temperature, pressure and odor, and by motor nerves that regulate secretions and blood flow. The nasal mucosa humidifies and warms the inspired air, hence it receives a large blood flow and the cells maintain a high degree of metabolic activity. Inflammation of the nasal mucosa caused by allergy, infections, or irritants and the like, will cause the mucosa to secrete fluids, swell, and obstruct. When the nasal membranes increase in volume, the area available through which air can pass is diminished, and therefore one experiences a sense of "stuffiness", resistance to inspiration, or a feeling of nasal obstruction. The nose can also become "runny" (rhinorrhea) and fluid accumulation and discharge add to the feeling of congestion. If either or both sides of the nose are obstructed, the asymmetry in airflow is perceived as an unpleasant condition.

The following descriptions give an over-view of some quantitative dimensions of nasal function. The normal air intake is about 10,000 liters per day and nasal secretions contribute about 30 ml of fluids to humidify each 1000 liters. The relative humidity of air inhaled via the nose is about 60% when it goes past the nose, but it is only about 5% when the air is breathed through the mouth. The relative humidity of air in the bronchi is 100% at body temperature and this humidification, contributed by blood flow through the mucosa, is required to maintain ciliary activity and prevent epithelial changes in the bronchial mucosa. Desiccation of the bronchial surface for more than 2 to 3 hours can cause mucosal changes that result in thickening of secretions, irritation, and increased susceptibility to infection.

Airflow into and out of the lungs is a function of:
AIRFLOW~FORCE/RESISTANCE
RESISTANCE~1/RADIUS$^4$
AIRFLOW~FORCE×RADIUS$^4$ Force for inspiration is the work done by the respiratory muscles to create negative intra-thoracic pressure and resistance is determined by the diameter of the airway and the viscosity of its contents. According to the Poiseuille equation, a small decrease in the radius of the airway is magnified to the fourth power and expressed as increased resistance to airflow. The nasal passages contribute 50% of the total resistance to overall airflow. Hence, any nasal congestion or obstruction will require greater effort to bring air to gas exchange surface in the lower respiratory tract.

Nasal stuffiness and congestion has many causes, the most common being "rhinitis", a technical term meaning the condition of inflammation of the membranes lining the nose. Rhinitis is characterized by nasal congestion, rhinorrhea ("runny nose"), sneezing, itching of the nose and/or post-nasal drainage. A common form of rhinitis is seasonal allergic rhinitis which is caused by an immunoglobulin E (IgE)-mediated reaction to seasonal aeroallergens. Typical seasonal aeroallergens are pollens and molds. The length of seasonal exposure to these allergens is dependent on geographic location. Perennial allergic rhinitis is caused by an IgE-mediated reaction to perennial environmental aeroallergens. These may include dust mites, molds, animal allergens, or certain occupational allergens, as well as pollen in areas where pollen is prevalent perennially. Allergic rhinitis frequently coexists with allergic conjunctivitis (of the eye) and is often present in individuals with asthma. Rhinitis can also be caused by food allergies. Some individuals, without evidence of allergic sensitization, will have rhinitis in reaction to nonspecific irritant stimuli such as cold dry air, perfumes, paint fumes, and cigarette smoke. This condition is called vasomotor rhinitis. Severe rhinitis may result from injury to the nasal membranes such as occurs after smoke inhalation, sinusitis, or after nasal surgery.

The rhinitis that is most familiar to everyone is infectious rhinitis caused by viruses such as the common cold virus. Initially, viral rhinitis is characterized by clear, watery rhinorrhea that is accompanied by sneezing and nasal obstruction. Edema of the nasal mucosa produces occlusion of the sinus ostia, with resulting facial pain, or of the Eustachian tube, with resulting ear fullness. The nasal drainage may become cloudy due to the presence of microorganisms and cellular debris. Responsible viruses include rhinoviruses, respiratory syncytial virus, parainfluenza, influenza and adenoviruses. Fever may accompany viral rhinitis, especially if there is bacterial superinfection by streptococcal organisms.

Rhinosinusitis, in which inflammation of the mucosa of the nasal sinuses occur together with the nasal membranes, is especially aggravating because it is accompanied by prolonged mucopurulent nasal discharge, facial pain and pressure, olfactory disturbance, and post-nasal drainage with cough. Conditions of the upper airways in which rhinitis is a component are described in detail by M. S. Dykewicz et al. (Diagnosis and management of rhinitis: Complete guidelines of the Joint Task Force on practice parameters in allergy, asthma and immunology. Annals Allergy Asthma Immunology 81: 478–518, 1998).

The time-course of the nasal response to irritants can be exactly chronicled in the laboratory. In patients with sensitivity, provocation with the allergen will result in an immediate response of severe sneezing, itching, hypersecretion and a moderate sense of obstruction. These events peak at 30 minutes and last for about 90 minutes after provocation. The immediate response is followed by the late and/or delayed response in which severe nasal congestion and a sense of obstruction is the primary symptom. The late response to a single challenge begins 4 hours after provocation, peaks at 8 hours, and fades at 12 hours. The delayed response begins at 24 hours after provocation, peaks at 36 hours and fades at 56 hours. During the peak time of late nasal obstruction, the nostril to nasopharynx pressure gradient rises by 20 to 24 cm of water as measured by rhinomanometry, illustrating the increase in airflow resistance caused by rhinitis.

Nasal stuffiness is an important contributory factor to other breathing disorders of the upper airways, such as snoring and sleep apnea, as reviewed by M. B. Scharf and A. P. Cohen (Diagnostic and treatment implications of nasal obstruction in snoring and obstructive sleep apnea. Annals Allergy Asthma Immunology 81: 279–290, 1998). As mentioned previously, airflow through the nasal passages contributes to 50% of respiratory resistance. When airflow is impeded, there must be compensatory increased respiratory force and mouth breathing commences. While individuals with nasal congestion may be capable of breathing through the nose while awake, they must exert more effort to draw air through the nasal airway during sleep because pharyngeal muscles relax during sleep and this relaxation narrows the airway passage in the back of the mouth. The additional respiratory effort produces a greater vacuum in the throat, which pushes the throat tissues, including the tongue, towards the pharynx and further reduces the space for airflow. Mouth breathing also reduces pharyngeal airspace and contributes to snoring and the related condition known as obstructive sleep disorder.

Snoring and obstructive sleep disorders (also called obstructive sleep hypoapnea/apnea) are breathing disorders of the upper airways. The pathophysiological bases of these disorders are described in many monographs and an excellent review by Scharf and Cohen (supra) is available for reference. Briefly, snoring consists of audible sounds produced during sleep caused by vibrations of throat muscles. The throat muscles vibrate more readily when they are relaxed during sleep and when air velocity is high. Obstruction of the pharynx by hypertrophied adenoids (tonsils) or obesity can also cause excessive snoring. J. M. Truelson in an eMedicine article provides an elegant description of the underlying mechanisms:

"Two basic principles of fluid flow can be applied to give some additional insight to the effects of airway narrowing—the Bernoulli principle and the Venturi effect.

The Bernoulli principle describes fluid flow in a column. A partial vacuum exists at the outer edges of a column of moving fluid such that the faster the flow, the greater will be the partial vacuum. The smaller the column, the faster the flow. An every day example of this is a paper straw. If you suck too hard on a straw, it collapses. If you suck less hard or the straw is more rigid, it does not collapse.

The Venturi effect deals with airflow accelerating as a current of air enters a narrow passageway. The wind blowing between buildings or water coming out of a hose partially occluded by the thumb are examples of this effect. Added to these effects are the distensible and moveable walls of the column of air in question—the pharynx.

Sleep apneics and normal individuals differ in their closing pressures and airway resistance due to the anatomy and the pliability of the walls of the pharynx. In a non-snoring adult the negative pressure required to close the upper airway is less than (more negative) −25 cm water. Snoring adults have a much more pliable airway, with closure during sleep occurring at pressures ranging from −2 to −10 cm water.

The cumulative effect of all these factors results in a vicious cycle, which eventuates in maximal airway closure permitted by the distensibility and relaxation of the airway. The cycle is only broken by arousal, disrupting the sleep."

Individuals with persistent snoring are not considered "normal" because snoring indicates some degree of airway obstruction. If snoring and sleep disturbances do not self-correct, the sleep disruption will cause fatigue, daytime sleepiness, short-term memory loss, decreased job effectiveness, and increased risk of motor vehicle accidents. The individual is less alert. There is also evidence of increased risk of heart attacks, strokes, high blood pressure, mood alteration, and sexual dysfunction in such individuals.

Ultimately, when airflow cannot be maintained by inspiratory force for any reason, the individual will progress to respiratory failure and the technical term describing the difficulty in breathing is "dyspnea." Dyspnea as a symptom is expressed as sensations of choking and suffocation. As a sign, it is expressed as labored breathing and inadequate ventilation with a rise in plasma carbon dioxide tension. Dyspnea occurs in serious disorders such as pneumonia, congestive heart failure, asthma, chronic obstructive pulmonary disease, emphysema, cystic fibrosis, muscular paralysis or dystrophy, Parkinson's disease, lung cancer, debilitation from wasting diseases and the like. The sense of suffocation, encompassed in dyspnea, is a frightening experience at the end of life.

Menthol, camphor and eucalyptus oil have been used since ancient times as remedies for nasal irritation and for refreshment of nasal sensations. These compounds are, however, not effective for rhinitis and may in fact exacerbate nasal congestion and obstruction, especially in the late and delayed stages of rhinitis. Sympathomimetic vasoconstrictors (decongestants) reduce nasal blood flow, but have a number of adverse side-effects, including rebound hyperemia (rhinitis medicamentosum). Disodium cromoglycate is effective for allergic rhinitis, but onset of effect is slow. By far, the most effective medications for seasonal, perennial and non-allergic rhinitis are the potent glucocorticosteroids administered as nasal sprays in manual pump-operated metered atomizers (e.g. Flonase®, Rhinocort®, Nasonex® and Nasocort®), as mouth or nasal inhalers or as nose-drops. These drugs reduce nasal membrane inflammation and the symptoms and signs of allergic rhinitis. These compounds do not, however, provide immediate sensory relief for nasal stuffiness, and are of limited efficacy for relieving the discomforts of infectious rhinitis and rhinosinusitis. Corticosteroids are effective in rhinitis associated with eosinophil-dominated inflammation (e.g. allergic rhinitis), but not in rhinitis associated with neutrophil-dominated inflammation (e.g. common cold, infectious rhinitis, sinusitis).

Spray mists and nose drops containing mixtures of herbal oils, including peppermint oil, are available as non-FDA regulated products for snoring, but no clinical evidence of efficacy for these preparations has been published in the medical literature. Mechanical devices for continuous positive airway pressure (CPAP) assisted breathing are available for severe snoring, obstructive sleep disorders, and for dyspnea from respiratory disorders. These devices are expensive and require patient cooperation.

BRIEF SUMMARY OF THE INVENTION

In one embodiment of the present invention, a composition is provided that comprises a 1-R1-phenyl, 4-R2-phenyl substituted 1,2,3,6-tetrahydropyrimidine-2-one cold receptor agonist formulated as a dry inhalable powder with a mean particle size diameter in the range of between about 50 μm to about 100 μm. The composition is usefully delivered in a therapeutically effective amount as particles to the lining of the upper airways. The cold receptor agonist is preferably represented by the general formula 1-[R1-phenyl]-4-[R2-phenyl]-1,2,3,6-tetrahydropyrimidine-2-one wherein: R1 is -hydroxy, a derivatized hydroxyl, -chloro, -fluoro, -alkyl (with about 2 to 4 carbons), -acetoxy, -trifluoromethyl; and R2 is -nitro, -chloro, -fluoro, -alkyl, -trifluoromethyl.

In another aspect of the present invention, an apparatus useful to relieve breathing disorders is provided that comprises a dispenser adapted to deliver at least one unit dose of a therapeutically effective composition to the upper airways. The composition within the dispenser preferably includes a cold receptor agonist having the formula 1-[R1-phenyl]-4-[R2-phenyl]-1,2,3,6-tetrahydropyrimidine-2-one wherein: R1 is -hydroxy, a derivatized hydroxyl, -chloro, -fluoro, -alkyl (with about 2 to 4 carbons), acetoxy, -trifluoromethyl; and R2 is -nitro, -chloro, -fluoro, -alkyl, -trifluoromethyl. The cold receptor agonist is preferably in an amount of at least about 1 mg per unit dose.

In yet another aspect of the invention, a therapeutic article, usefully administered for relieving breathing disorders, comprises a plurality of discrete doses of cold receptor agonist. A particularly preferred cold receptor agonist embodiment for practicing this, and all aspects of this, invention is called "icilin".

Practice of this invention provides improved therapeutic benefit for the treatment of breathing disorders of the nose and throat, such as sensations of nasal obstruction and snoring. Thus, for example, a particularly preferred method of treating nasal stuffiness in a human comprises intranasally administering droplets or particles of a composition comprising 1-[2-hydroxyphenyl]-4-[3-nitrophenyl]-1,2,3,6-tetrahydropyrimidine-2-one or an analog, preferably wherein the 1-[2-hydroxy]-4-[3-nitrophenyl]-1,2,3,6-tetrahydropyridimine-2-one or an analog is preferably in an amount of at least about 5 to 100 mg of the composition, more preferably about 10 mg of the composition.

The further advantages and aspects of the present invention will be understood by reading the following detailed description and the accompanying claims.

DETAILED DESCRIPTION OF INVENTION

In accordance with practice of the present invention, a cold receptor agonist, delivered directly to the upper airways, offers unique advantages for the symptomatic relief of breathing disorders. In the context of the present invention, I define relief of breathing disorders in the upper airways as a decrease in the sensations of nasal stuffiness, congestion, and obstruction (caused primarily by rhinitis), as inhibition of persistent snoring and related sleep disorders, and as alleviation of dyspnea; the primary effect being easier breathing, and relief from the sense of suffocation and choking. The articles, compositions and methods of this invention are useful for symptomatic relief of these breathing disorders.

Articles (and apparatus), compositions and therapeutic methods in accordance with this invention utilize a 1-R1-phenyl, 4-R2-phenyl substituted 1,2,3,6- tetrahydropyrimidine-2-one cold receptor agonist, preferably of the general formula 1-[R1-phenyl]-4-[R2-phenyl]-1,2,3,6-tetrahydropyrimidine-2-one wherein: R1 preferably is -hydroxy, derivatized hydroxyl, -chloro, -fluoro, -alkyl (with about 2 to about 4 carbon atoms) -acetoxy, -trifluoromethyl; and R2 preferably is -nitro, -chloro, -fluoro, -alkyl (with about 2 to 4 carbons), or -trifluoromethyl, more preferably nitro or trifluoromethyl on R2. I refer to the particularly preferred compound shown below by Formula 2 as "icilin". Icilin analogs (as well as icilin) as illustrated by the Formula 1 general formula.

By "analogs of icilin" I further mean that the compounds have similar chemical and physical properties to icilin, particularly that they are also cold receptor agonists and thus are therapeutically effective when delivered in accordance with the invention. These similar chemical and physical properties of the Formula 1 analogs can be readily determined without undue experimentation by either screening for the "wet shaking" behavior in animals described by the Wei articles cited in the Background section and/or by screening for the activation of cation currents in cells transfected with the cold-menthol receptor (or related members of the TRP family), as also described in the Background section. That is, these icilin analogs are included within the scope of this invention.

Icilin is a lemon yellow crystalline powder with a molecular weight of 311 Daltons and a melting point of 229 to 231° C. The term "iclin" and "icilin analogs" as used herein includes the free base form of this compound as well as pharmacologically acceptable acid addition salts thereof. In addition to the free base, the addition salts include the hydrochloride, the hydrobromide, the hydroiodide, the bisulfate, the phosphate, the acide phosphate, and the like. The icilin analogs in powder form are without odor and non-irritating, meaning that it does not elicit any smell or unpleasant sensations upon contact with the surfaces of the human body. The compound is stable at room temperature. Icilin is readily soluble in organic solvents such as dimethylsulfoxide, nitromethane, dimethylacetamide and, after warming, in propanediols; slightly soluble in ethanol and acetone; and virtually insoluble in water. Thus, icilin would be considered as a lipophilic, hydrophobic compound that is not easily miscible with aqueous systems.

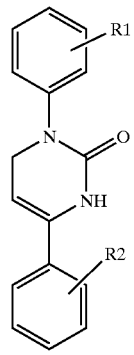

Formula 1: 1-R1-phenyl, 4-R2-phenyl, substituted 1,2,3,6-tetrahydropyrimidine-2-one.

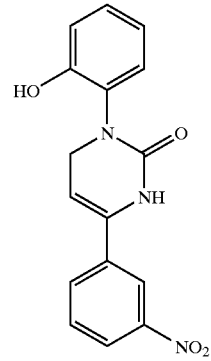

Formula 2: Icilin, 1-[2-hydroxy]-4-[3-nitrophenyl]-1,2,3,6-tetrahydropyridimine-2-one.

Methods suitable for the preparation of the Formula 1 and Formula 2 compounds are described by Podesva and Do Nascimento, U.S. Pat. No. 3,821,221, issued Jun. 28, 1974, incorporated herein by reference, and are exemplified by Example A hereinafter. As earlier noted also, icilin has recently become commercially available.

In the parent application, of which this is a continuation-in-part, I describe how icilin inhaled via the nose 0.5 mg or 2 mg (on separate occasions) of icilin in powder form produced a sensation of increased airflow, refreshment and coolness, without any odor or sense of irritation. No odor was detected, but after drug administration, a sense of free and unobstructed airflow in the nasal cavity was experienced for about 3 hours. Under identical circumstances, the inhalation of menthol crystals also produced a cooling and refreshing sensation but was accompanied by a mint flavor and an initial burning sensation. The duration of the menthol cooling effect that was achieved with 0.8 mg of menthol was 25 to 30 minutes. No overt beneficial effects of menthol were observed on the degree of nasal discharge or the urge to sneeze. Also, the eyes watered from the stinging sensations of menthol. From these experiments, it was concluded that icilin and its analogs have a refreshing action on the nasal surfaces that is not accompanied by odor or irritation and that the duration of action of icilin was longer than that of menthol.

I further report here that icilin and icilin analogs, administered at higher doses in powder and/or droplet (e.g. aerosolized) form, have a super-robust effect on nasal stuffiness. The period of action on nasal sensations, from a dose of 10 to 20 mg of icilin, exceeded 8 to 10 hours, the duration of normal sleep. Further, after inhalation of icilin, snoring was not observed for 3 days in an individual who normally suffered from this condition. The individual also reported that he slept smoothly through the 3 nights and felt refreshed, and did not have episodes of gurgling or choking sensations in his sleep that, on previous occasions, caused awakening. However, without continued use of icilin these signs and symptoms returned afterwards. Icilin, administered as a mist sprayed to the back of the throat, also had some beneficial effects on snoring and sleep, but the powder form of drug administration appeared to be more efficacious. Yet further the effect of the icilin on the nose is dependent on the particle size of the inhaled material. If the particles are small, viewed as fluffy and fine, the effect was much less effective than if the powder is agglomerated and visibly coarse. The preferred mean particle size is in a range of between about 50 $\mu$m to about 100 $\mu$m in mass median diameter. The lower value approaches a size that will remain suspended in air and not lodge onto receptors in the mucous membranes of the upper airways. The higher value approaches a size that will tend to sediment and not be easily suspended in air, and thus is less preferred.

Biological mechanisms of iIcilin action on the upper airways. Without being bound by theory, I wish to describe what I believe are the mechanisms underlying the actions of icilin and its analogs in relieving the sensations of nasal stuffiness, congestion and obstruction, snoring and dyspnea. At first, one might hypothesize that the effects of icilin analogs on cold receptors on nerve endings may generate sensations that mask the signals of fullness and distension that accompanies nasal congestion. That is, the cold sensations of icilin over-ride the other sensory inputs. But this view is not likely to be correct because inhalation of menthol or inhalation of very cold air, which would increase sensations of cold, have limited beneficial effects on nasal stuffiness in clinical situations.

The nasal mucosa is densely innervated because it regulates the temperature and humidification of air. The nerve endings release transmitters, such as acetylcholine, and neuropeptides, such as substance P, that, together with cells of the immune system, control blood flow and participate in the inflammatory response. One particular receptor on the sensory nerve ending, called the vanilloid receptor (capsaicin receptor 1, VR1), is linked to pain and warmth. Stimulation of the vanilloid receptor can lead to release of vasodilatory substances and inflammatory mediators such as histamine, substance P, calcitonin-gene related peptides, and cause mast cell degranulation. This process is called neurogenic inflammation. Babes et al. [Cooling inhibits capsaicin-induced currents in cultured rat dorsal root ganglion neurones. Neurosci Lett 317: 131–134,2002] showed that reducing the temperature in dorsal root ganglion neurones inhibited discharge of the vanilloid receptor. I believe that the actions of icilin may be explained by inhibition of neurogenic inflammation in the upper airways. Icilin may mimic the cold inhibition of vanilloid receptor activity and hence reduce neurogenic inflammation in mucous membranes. It is known that icilin rapidly desensitizes the sensory nerve ending to further stimulation (McKemy et al., supra). This may be the neurophysiological basis for its inhibitory actions of neurogenic inflammation. The process of neurogenic inflammation contributes to and exacerbates the signs and symptoms of asthma as well as the symptoms of rhinitis, bronchitis, and other respiratory disorders. [Barnes P J. Neurogenic inflammation in the airways. Respiratory Physiol 125: 145–154, 2001]. Hence reduction of neurogenic inflammation by icilin may also be beneficial in these conditions.

The beneficial effects of icilin and icilin analogs on snoring and on dyspnea may be simply explained on psychological grounds. Nasal airflow accounts for 50% of total airway resistance. If icilin analogs reduce nasal stuffiness, the brain, which "sees" the organism as a whole, may conclude that airflow is adequate and hence reduce inspiratory effort. A reduction in inspiratory effort will decrease snoring. Similarly, subjective feelings of choking and suffocation in the dyspneic patient may be attenuated if airflow from the nasal passages is perceived as plentiful and adequate for ventilation. It should be noted, however, that the mucosae of the upper airways have many intrinsic reflexs as well as integrative reflexs in the brainstem. Local cold sensory signals, initiated by icilin compounds applied as a spray mist to the pharynx, may, for example, trigger pharyngeal muscle contractions. Such contractions will widen the oropharynx aperture, decrease respiratory resistance, and reduce snoring. Local cold sensory signals may also inhibit signal traffic of mechano-insufflation receptors located in the upper airways, and hence decrease the signals that generate sensations of choking and suffocation.

Delivery to receptors in the nose and throat. In one embodiment of this invention, an apparatus useful to relieve breathing disorders comprises a dispenser adapted to deliver at least one unit dose of a therapeutically effective, inventive composition to the upper airways. This delivery may be in the form of droplets or particles. By "droplets" I mean to include aerosols and liposomes.

For delivery through the nose the pharmaceutical compositions of this invention may be administered by nasal drops, by nasal aerosols, or as an inhaled powder so that the therapeutically effective icilin or icilin analog composition reaches the mucosal surfaces. Nasal spray drug products are familiar items in the drugstore and in the prior art. For example, R. G. Achari et al. describe the formulation of apomorphine for nasal delivery U.S. Pat. No. 6,436,950, incorporated herein by reference. The formulations may be gels, suspensions, liposomal dispersions, emulsions, microemulsions and combinations thereof. The formulated product contains active ingredient (icilin analogs) dissolved or suspended in solutions or mixtures of excipients (e.g., preservatives, viscosity modifiers, emulsifiers, buffering agents). A non-pressurized manual pump dispensers may be used to deliver a spray containing a metered dose of the active ingredient. The dose can be metered by the spray pump or could have been pre-metered during manufacture. A nasal spray unit can be designed for unit dosing or can discharge up to several hundred metered sprays of formulation containing the drug substance. Nasal sprays are applied to the nasal cavity for local and/or systemic effects.

Suitable nasal spray formulations of inventive compositions can be readily prepared according to techniques well known in the art of pharmaceutical formulation. For example, the preparation of solutions or emulsions are described by Achari et al., U.S. Pat. No. 6,436,950 (supra), J. G. Nair [Chapt. 39, Solutions, Emulsions, Suspensions and Extracts, pg. 721–752J] and aerosols by J. Sciarra and C. J. Sicarra [Chapt. 50, "Aerosols", pg. 963 to 979] in the standard text: "Remington, the science and practice of pharmacy," Alfonso R. Gennaro, Chairman of the editorial board and editor. 20th ed. Baltimore, Md. Lippincott Williams & Wilkins, 2000.

The icilin compositions may be prepared as gels, liposomal dispersions, suspensions or emulsions in saline, employing benzyl alcohol, benzalkonium chloride or other suitable preservatives, absorption promoters such as cyclo-dextrins to enhance bioavailability and bioadhesives for prolonged contact, and/or other solubilizing or dispersing agents known in the art. Thus, a composition for administration to the intranasal surfaces is particularly contemplated that comprises a solution of icilin dissolved or dispersed in a pharmaceutically acceptable diluent (carrier). The solvent or wetting agent may be propylene glycol (1,2-propanediol) and a variety of aqueous carriers can be used, e.g. buffered water, 0.9 percent saline, buffered aqueous-ethanol solutions and the like. These compositions can be sterilized by conventional, well-known sterilization techniques, or can be sterile filtered. The resulting solutions can be packaged for use as is or mixed as an adjuvant to another medication.

The inventive embodiment compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

An example of a suitable nasal mist in which icilin or an icilin analog is added is Ayr® Saline Nasal Mist, which is an isotonic saline (sodium chloride) solution, buffered with sodium phosphate, and preserved with disodium EDTA and benzalkonium chloride. An example of a suitable nasal spray decongestant to which icilin or an icilin analog may be added is Afrin® Severe Congestion Nasal Spray with Menthol, a product of Schering-Plough, Inc. The active ingredient in this nasal spray is oxymetazoline hydrochloride (0.05%), a sympathomimetic amine vasoconstrictor decongestant, and the inactive ingredients are listed as benzalkonium chloride, benzyl alcohol, camphor, edetate disodium, eucalyptol, menthol, polysorbate 80, propylene glycol, sodium phosphate dibasic, sodium phosphate monobasic, and water. Another product, or carrier, for inventive icilin compositions is Vapor Inhaler® (levamphetamine, as a nasal decongestant), a product of Vicks Corporation, a division of Proctor and Gamble. The Inhaler is recommended for upper respiratory ailments, such as the common cold, cough and bronchitis. The inclusion of icilin compounds and compositions to such nasal sprays, mists and aerosols so that the inventive compositions are delivered as droplets will provide improved treatment of rhinitis and nasal discomfort.

If the goal of treatment is to relieve nasal stuffiness from rhinitis and to produce a sensation of increased airflow in the nose, the dose of icilin compounds required would be about 1 to 10 mg per application, and the volume of intranasal delivery less than 1 ml. Thus, the concentration of icilin utilized would be usually at least about 0.5 percent to as much as about 5 percent by weight. The selection of fluid volumes would be in accordance with the particular mode of administration selected and the presence of adjuvants. Thus, a typical pharmaceutical composition for delivery can be made up to contain about 0.25 mg/ml to about 150 mg/ml of the icilin, and more preferably at 5 to 50 mg/ml. For nasal/mouth sprays or mists, a manual pump-activated spray using air as propellant (atomizer or nebulizer) is contemplated as a suitable dispenser. If used in combination with menthol or menthol analogs, the prefered molar ratio of icilin to menthol or menthol analog is about 1 to 1, with a range of 1 to 0.5, 2 to 1, and 3 to 1.

Access of icilin compounds to the target cold receptors may be impeded by mucopurulent contents on the nasal membranes in situations of severe nasal congestion and obstruction, such as a viral cold super-infected with Streptococci, or as in rhinosinusitis. In such conditions, icilin compounds may be formulated at a higher concentration, e.g. 50 mg/ml, together with a mucolytic such as N-acetyl-cysteine (Solmucol®) or a surfactant to enhance drug delivery. Examples of surfactants are the esters or partial esters of fatty acids containing from 6 to 22 carbon atoms, such as octanoic, palmitic, stearic, linoleic, and oleic acids with an aliphatic polyhydric alcohol or its cyclic anhydride such as, for example, ethylene glycol, glycerol, glycerin, erythritol, arabitol, mannitol, sorbitol, and the polyoxyethylene and polyoxypropylene derivatives of these esters and the like. Mixed esters, such as mixed or natural glycerides can also be employed. The surfactant can constitute about 0.1 to about 20 percent by weight of the composition, and preferably about 0.25 to about 5 percent.

Another form of delivery of icilin to the nasal cold receptors is to administer icilin in powder form; by itself or admixed to an inert carrier such as calcium carbonate or lactose. Methods for preparing spray dried powder with a hydrophilic excipient, e.g. povidone, lactose, and delivering it using dry powder nasal inhalers, have been described by Gordon et al. (U.S. Pat. No. 6,365,190) and are incorporated herein by reference. The advantage of a powder method for icilin delivery is that it may have a more prolonged action when administered in dry powder versus in soluble forms, as the nose has robust clearance mechanisms. The powder form icilin may be prepared in micronized form, by re-crystallization, by granulation, by drying, or by milling to a specified particle size and thus to have a high surface area for interaction with cold receptors. Methods for preparing powders are well-known to the art and have been reviewed by R. E. O'Connor and J. B. Schwartz (Powders, Chapt. 37, pg. 681–699) in the standard text: "Remington, the science and practice of pharmacy," Alfonso R. Gennaro, Chairman of the editorial board and editor. 20th ed. Baltimore, Md. Lippincott Williams & Wilkins, 2000. To quote from this Chapter (pg. 688):

"Sieving is one of the simplest and probably most frequently used methods for determining particle-size distribution. The technique basically involves size classification followed by the determination of the weight of each fraction.

In this technique, particles of a powder mass are placed on a screen made up of uniform apertures. By the application of some type of motion to the screen, the particles smaller than the apertures are made to pass through. The sieve motion generally is either 1) horizontal, which tends to loosen the packing of the particles in contact with the screen surface, permitting the entrapped subsieve particles to pass through, or 2) vertical, which serves to agitate and mix the particles to the screen surface.

Industrial-sized mechanical sieves are varied in design and capacity, and include the gyratory, circular rotatory, vibrating, shaking, and revolving sifters. In gyratory sifters, the motion is in a single horizontal plane, but may vary from circular to reciprocal from the feed to the discharge end. The circular sifter also confines the screen motion to a horizontal plane, but in this case the total motion applied to the sieve is circular. The materials enters the top of a gyratory sifter and spreads over the first sieve. Some of the finer particles drop through and are discharged into the throughs channel. The remaining powder moves to the next sieve in order, the process is repeated until complete separation is accomplished.

In centrifugal screening, the material is pushed through a spinning vertical wire cloth cyliner. Sharp cuts in particle size can be obtained by this type of equipment."

The dry powder form of delivery is particularly preferred in situations where upper respiratory inflammation and breathing distress is a severe medical condition such as in smoke inhalation, pain from nasal surgery, severe nasal congestion, rhinitis complicated by asthma, intractable snoring with episodes of sleep apnea, and acute dyspnea. A powder form of drug delivery permits a prolonged and robust pharmacological action.

Many commercial inhalers are available for drug delivery to the nose and mouth, and are suitable as dispensers for delivering at least one unit dose of the inventive icilin compositions. Aerosols are defined as colloidal systems of very finely subdivided liquid or solid particles dispersed in and surrounded by a gas. The standard aerosol inhaler is the metered-dose inhaler (MDI), consisting of an aerosol unit and plastic mouthpiece. This is currently the most common type of inhaler, and is widely available. The 3M Company manufactures an "autohaler" which is a MDI activated by one's breath, and doesn't need the breath-hand coordination that a regular MDI does. The primary use of these MDI is drug treatment of asthma.

Dry powder inhalers are mainly designed for oral administration. For one example, an inhaler available from Glaxo Wellcome called the Accuhaler Serevent contains a foil strip with 60 blisters, each containing one dose of an asthma drug. Pressing the lever punctures the blister, which allows the drug to be inhaled through the mouthpiece. Another dry poweder inhaler called the Serevent Diskhaler from GlaxoSmithKline has drug kept in a series of little pouches or blisters on a disk; and when the pouches are punctured drug may be inhaled through the mouthpiece. Yet another dry powder inhaler, also available from GlaxoWellcome, is the Rotahaler used with Ventolin Rotacaps capsules. Each capsule contains one dose of a glucocorticosteroid. The user operates the inhaler so as to open the capsule. The powder may then be inhaled through the mouthpiece. Yet another example is the Turbohaler dry powder inhaler. The drug is in form of a pellet. When the body of inhaler is rotated, a discrete dose of drug is ground off the pellet. The powder is then inhaled through a fluted aperture on top. All these dry powder inhalers function to administer drug via the mouth.

An insufflator (designed to blow drug into the body cavity) is a dry powder nasal inhaler used with Rynacrom (disodium cromoglycate) cartridges. Each cartridge contains one dose. The inhaler is operated to open the cartridge to allow the powder to be blown into the nose by squeezing the bulb.

All of the just described dry powder inhalers are suitably and readily adapted to practicing this invention. The last noted, nasal inhaler, is especially well suited for adaptation as a drug delivery system for the icilin compounds.

Thus, another embodiment of the present invention is wherein a therapeutic article comprises a plurality of discrete icilin or icilin analog doses, with each dose being therapeutically effective when administered to the upper airways lining, via a nasal or oral inhaler, so as to relieve breathing disorders. These discrete doses of a dry powder icilin composition may be packaged as capsules, pellets, blisters, pouches or the like in an analogous manner to the just-described asthma drugs that are usefully delivered by the various known dry powder inhalers.

The physical forces of inertial impaction and sedimentation govern the deposit of inhaled particles on the nasal membrane surface. The inertia of an airborne article will cause it to travel in its initial path when the supporting airstream is suddenly deflected (as in the bifurcations of the nasal turbinates). These particles will then impact and adhere to the nasal membranes. Large particles will also sediment due to gravity. Thus, particles having diameters in the range of about 50 to 100 $\mu$m are readily trapped in the nasal vestibule, whereas smaller particles are carried by the airstream in suspension and diffuse to the lower airways. In formulating an icilin compound for nasal or mouth administration in accordance with the invention, one preferably prepares a powder with particle sizes that are greater than about 50 $\mu$m. The particle geometry, roughness, density, and size distribution should then be optimized to create the proper adhesion forces between particles so that the delivery system does not cause agglomeration of the particles or adhesion of the particles to the walls of the delivery device.

Recent Food and Drug Administration guidelines on nasal sprays and mists recognize that there may be considerable interactions between extraneous ingredients and the active drug. These guidelines require extensive tests of analytical purity and compatibility of mixtures, which adds to the costs of development. In practicing this invention, I prefer to minimize or avoid the use of vehicle, excipients or preservatives, and the like, in the formulations. Thus, a preferred method of preparation is to take the purest form the drug (e.g., greater than 99% purity), grind and sieve the powder for an optimal particle size distribution that is larger than about 50 $\mu$m in mass median diameter, and insert this powder into either a plurality of discrete, sterile disposable cartridges each of which is suitable for unit dosing or a single cartridge for unit dosing. Such a single disposable cartridge may be, for example, a conical specific volume dispenser, with a container having side-walls squeezable in a radial direction to a longitudinal axis in order to dispense the container contents therefrom at one end of the container. Such disposable containers are currently used to dispense eye-drops at 0.3 to 0.4 ml (e.g. Lens Plus® and Refresh Plus®) per unit dosing, and are ideally adaptable for the nasal delivery of icilin powders. Examples of such unit volume dispensers for medications arc described by W. S. Iba, U.S. Pat. No. 5,582,330, I. L. Britto et al. U.S. Pat. No. 6,098, 619, A. R. Lockhart et al. U.S. Pat. No. 6,443,152 and R. S. Dirksing, U.S. Pat. No. 5,215,221, all incorporated herein by reference.

The unit dose of icilin compounds for each container may vary from 1, 2, 5, 10, or up to 25 mg, depending on the size of the patient's nasal vestibule and the clinical condition to be treated. It is anticipated that the higher doses may be required to treat more severe forms of breathing disorders.

The nasal route of administration will deliver the icilin compounds to the nasal membranes and to the upper portions of the pharynx. But this mode of administration may not be adequate to deliver sufficient dose in severe cases of snoring and sleep apnea, and in chronic dyspnea, since recruitment of sensory receptors in the back of the pharynx or the upper trachea may also be important for inhibition of noxious sensory signals from nerve endings. In such instances, it may be beneficial to provide a mouth spray containing icilin compounds. Such mouth sprays may be formulated as the nasal sprays and mists described above.

In summary, I believe that no investigations of icilin in human breathing disorders have been reported in the scientific literature other than what is discussed or described here. I point out the unique properties of icilin and describe novel compositions and preferred embodiments for therapeutic methods of use in breathing disorders.

In the below experimental section, Example A describes a preparation of icilin, while Examples 1 to 5 describe therapeutic uses of the invention with human subjects.

EXPERIMENTAL

EXAMPLE A

Chemical Synthesis of Icilin and Analogs. The methods of chemical synthesis are as described by Podesva and Do Nascimento U.S. Pat. No. 3,821,221. Briefly, a substituted acetophenone, e.g. 3-nitroacetophenone or 3-trifluoromethylacetophenone, readily obtainable from commercial sources such as Sigma-Aldrich, Co., is mixed with diethylamine or dimethylamine in formaldehyde and refluxed in acidic solutions. After addition of a second substituent, the Mannich reaction produces a β-aminoketone compound which is isolated. This reagent is then reacted with potassium cyanate or sodium cyanate to produce an unstable urea intermediate that proceeds to cyclize into the tetrahydropyrimidine-2-one ring, with the appropriate groups on position 1 and 4 of the 1,2,3,6-tetrahydropyrimidine-2-one ring. The precipitated product is readily collected by filtration and is recrystallized using solvents such ethyl acetate, and purity is assessed by high-performance liquid chromatography. The final products are solids stable at room temperature

EXAMPLE 1

Three normal healthy subjects volunteered to inhale via the nose 5 mg of icilin in powder form. This powder was agglomerated (available from Phoenix Pharmaceuticals, Belmont, Calif., USA) and had a particle size distribution of greater than 50 μm in diameter. No odor was detected. After drug administration, a sense of free and unobstructed airflow in the nasal cavity was experienced for about 5 hours, with punctate sensations of cold at discrete locations in the nose. The sensations were described as soothing, cooling and refreshing. Under identical test conditions, one subject inhaled 8 mg of icilin powder obtained from Tocris Cookson, Inc. (Ellisville, Mo. 63021). This powder was fluffy, easily became airborne, and had a particle size distribution of less than 50 μm in diameter. Cooling sensations were felt after inhalation, but more from the upper lip than from inside the nostrils. The cooling and soothing sensations from the nasal vestibule were of short duration after the Tocris icilin and lasted less than 30 minutes. These experiments demonstrate that icilin delivered to the nasal vestibule has cooling actions. Furthermore, the duration of action is dependent on the particle size of the inhaled powder.

EXAMPLE 2

A male subject, suffering from seasonal allergic rhinitis, had severe nasal congestion and obstruction, which was not relieved by taking two antihistamine Allegra® tablets. He was a habitual snorer and had episodes of abrupt awakenings in the early morning hours. This individual inhaled 20 mg (in two dose applications of 10 mg each) of icilin in powder form. The icilin powder was placed on the back of his hand and sniffed vigorously. No odor was detected. After drug administration, a sense of free and unobstructed airflow in the nasal cavity developed within 15 minutes and the effect lasted for more than 8 hours. This individual then repeated the experience 5 days later. His wife then noted that he stopped snoring and snorting during sleep for the next 3 days after icilin administration. Furthermore, the individual felt refreshed and invigorated by undisturbed sleep during this time. As mentioned previously, this individual had episodes of abrupt awakening in the early morning hours with sensations of choking and making gurgling sounds that would awaken his wife. These episodes did not occur during the 3 days after icilin inhalation.

EXAMPLE 3

A male subject suffered from perennial rhinitis that was aggravated when his daughter's dog came to visit and stayed on his bed to sleep. The individual's nasal membranes felt stuffed up, irritated, and burning, and falling asleep was difficult because he felt that he could not breathe. Mouth breathing was not comfortable, and the individual then begin taking a benzodiazepine sedative to go to sleep. However, the sedative and the restless sleep made the individual tired the next day and he could not maintain his concentration at work. This individual was then given a 5 mg dose of icilin, placed in a small plastic tube, and instructed to inhale the powder before going to sleep. He reported that airflow in the nose was smooth and cool after icilin intake and his sense of nasal stuffiness was significantly reduced. He had a good night's sleep and felt refreshed the next day.

EXAMPLE 4

An icilin solution was prepared using 10% icilin dissolved in propylene glycol and mixed 1:5 with sterile water to yield a 2% icilin concentration. The solution was placed in an empty 10 ml bottle with a digital plunger and nozzle valve (Migra Spray® bottle). The aerosol spray of icilin, when applied several times into the back of the mouth, produced the characteristic sensations of cold. This experiment shows that there are icilin-type receptors at the back of the throat that can be activated by delivery of the drug via a mouth spray.

EXAMPLE 5

An icilin solution was prepared using 10% icilin dissolved in propylene glycol and mixed 1:5 with Ayr® Saline Nasal Mist to yield a 2% concentration. Ayr® Saline Nasal Mist is an isotonic saline (sodium chloride) solution, buffered with sodium phosphate, and preserved with disodium EDTA and benzalkonium chloride. The bottle of Ayr® Saline Nasal Mist had a volume of 50 ml and had a nozzle for dispensing a nasal mist. The icilin-saline spray mist was applied intranasally to a subject with nasal congestion from seasonal allergic rhinitis. Sensations of coolness were experienced and the sense of nasal of obstruction was relieved.

From these experiments, it is concluded that icilin and its analogs applied as a powder or as a nose/mouth spray have 1) a prolonged cooling and refreshing action on the nasal and throat surfaces that is not accompanied by odor or irritation, 2) a action on the nasal mucosa that relieves the sensations of obstruction, and 3) an ability to suppress snoring and facilitate sleep, and to suppress sensations of choking and suffocation.

It is to be understood that while the invention has been described above in conjunction with preferred specific embodiments, the description and examples are intended to illustrate and not limit the scope of the invention, which is defined by the scope of the appended claims.

What is claimed is:

1. A method of treating airway obstruction in a mammalian patient comprising: administering via the nose or throat a therapeutically effective amount of a cold receptor agonist having the formula 1-[R1-phenyl]-4-[R2-phenyl]-1,2,3,6-tetrahydropyrimidine-2-one wherein R1 is hydroxy, chloro, fluoro, an alkyl of about 2 to about 4 carbon atoms, acetoxy, or trifluoromethyl and R2 is nitro, chloro, fluoro, an alkyl of about 2 to 4 carbon atoms or trifluoromethyl.

2. The method as in claim 1 wherein the agonist is administered by inhalation as a powder.

3. The method as in claim 1 wherein the administering includes flowing the agonist through the air as particles or droplets and into contact with the patient's upper airway.

4. The method as in claim 1 wherein the agonist administered further includes an agent selected from the group consisting of an anti-inflammatory glucocorticosteroid, a local anesthetic, a sympathomimetic amine decongestant, an anti-histamine, a local anesthetic, menthol or a menthol analog and mixtures thereof.

5. The method as in claim 2 wherein the agonist is administered in an amount of at least about 1 mg per application.

* * * * *